(12) United States Patent
Shakespeare et al.

(10) Patent No.: US 6,538,743 B2
(45) Date of Patent: Mar. 25, 2003

(54) METHOD AND APPARATUS FOR MEASURING PROPERTIES OF PAPER WEB

(75) Inventors: John Shakespeare, Siuro (FI); Markku Mänty, Kangasala (FI); Matti Kukkurainen, Tampere (FI)

(73) Assignee: Metso Automation Oy, Helsinki (FI)

( * ) Notice: Subject to any disclaimer, the term of this patent is extended or adjusted under 35 U.S.C. 154(b) by 0 days.

(21) Appl. No.: 09/997,714

(22) Filed: Nov. 29, 2001

(65) Prior Publication Data

US 2002/0085201 A1 Jul. 4, 2002

Related U.S. Application Data

(63) Continuation of application No. PCT/FI00/00523, filed on Jun. 9, 2000.

(30) Foreign Application Priority Data

Jun. 11, 1999 (FI) .................................... 991346

(51) Int. Cl.[7] .............................................. G01N 21/84
(52) U.S. Cl. ...................................................... 356/429
(58) Field of Search ........................... 356/71, 428, 430, 356/431; 250/556, 223 R

(56) References Cited

U.S. PATENT DOCUMENTS

| | | | |
|---|---|---|---|
| 4,565,444 A | | 1/1986 | Mactaggart |
| 4,587,434 A | * | 5/1986 | Roes et al. .................. 250/556 |
| 4,801,809 A | | 1/1989 | Burk et al. |
| 5,073,712 A | | 12/1991 | Hellstrom |
| 5,327,770 A | | 7/1994 | Hindle |
| 5,440,386 A | | 8/1995 | Campas |
| 5,625,196 A | | 4/1997 | Williams |
| 5,923,413 A | * | 7/1999 | Laskowski .................... 356/71 |
| 6,172,745 B1 | * | 1/2001 | Voser et al. .................. 356/71 |

FOREIGN PATENT DOCUMENTS

| | | |
|---|---|---|
| DE | 19646888 | 4/1998 |
| EP | 0 154 722 B1 | 9/1985 |
| EP | 0 522 711 B1 | 12/1998 |

* cited by examiner

Primary Examiner—Michael P. Stafira
(74) Attorney, Agent, or Firm—Alston & Bird LLP

(57) ABSTRACT

A method and an apparatus for measuring properties of a paper web, whereby at least one property of the paper web is measured at least at two locations in the cross direction of the paper web simultaneously. Adjacent measuring devices are calibrated by traversing a reference sample in the cross direction such that the reference sample is impinged by the measuring beam from each of the measuring devices.

29 Claims, 2 Drawing Sheets

METHOD AND APPARATUS FOR MEASURING PROPERTIES OF PAPER WEB

CROSS-REFERENCE TO RELATED APPLICATION

This application is a continuation of International Application No. PCT/FI00/00523 filed Jun. 9, 2000, which application was published in the English language.

FIELD OF THE INVENTION

The invention relates to a method for measuring properties of a paper web, in which method at least one property of the paper web is measured with at least one measuring means that transmits a measuring beam at least on one measuring channel such that at least two locations in the cross direction of the paper web are measured simultaneously.

The invention further relates to an apparatus for measuring properties of a paper web, the apparatus comprising at least one measuring means having means for transmitting a measuring beam at least on one measuring channel, whereby the apparatus is arranged to measure at least one property of the paper web by measuring at least on two adjacent measuring channels in the cross direction of the paper web simultaneously.

BACKGROUND OF THE INVENTION

It is known to measure properties of a moving paper web with a measuring device such that a measuring point of a measuring sensor traverses in the cross direction of the paper web. The measuring sensor is generally secured to a measuring bar positioned across the paper web. It is also known to use so-called optical traversing in measuring the properties of the paper web as disclosed in U.S. Pat. No. 5,073,712. In this method, a measuring sensor is fixedly mounted above the web and a measuring beam to be transmitted from the sensor traverses the web in the cross direction. Calibration of these measuring devices is carried out in such a way, for instance, that a reference sample is placed e.g. at the edge of the paper web, outside the web, and the measuring device measures the properties of said reference sample at suitable intervals, and on the basis thereof, calibrates the measuring means in a manner known per se. However, in the solution concerned, the measuring device measures the paper web diagonally, whereby measuring results will not be obtained from adjacent locations, for instance. The measuring method is also relatively slow.

To speed up a measurement and to obtain adjacent measuring results, it is known to use solutions, in which the paper web properties are measured simultaneously at adjacent measuring points. Solution of this kind are disclosed, for instance, in U.S. Pat. Nos. 4,565,444 and 4,801,809. Further, the publication by Pertti Puumalainen "Paperikoneen CD-mittausten tulevaisuudennäkymät, Paperirataa on-line mittaavat laitteet ja niihin liittyvät säädöt, Feb. 24–25, 1998, Lappeenranta"(The prospects of paper machine CD measurements, Devices measuring the paper web online and adjustments related thereto, Feb. 24–25, 1998, Lappeenranta) sets forth a solution in which a plurality of measuring devices are adjacently positioned and each measuring device is moved back and forth for a portion of the paper web in the cross direction. Thus each sensor analyzes a small portion of the paper web width. However, calibration is very difficult in these solutions. In the above-mentioned publication by Puumalainen, a reference sample is placed above each measuring device, and for calibration, the measuring bar, onto which the measuring devices are placed, is turned upside down such that each measuring device then measures the values of the reference sample locating in front of the measuring device concerned. However, a problem with this solution is that various reference samples may originally be different or they may become different due to aging or various outside influences, such as fouling, and consequently the measuring devices are calibrated onto different levels, i.e. their readings become different. The structure of the solution in question is also very complicated and hence cumbersome and expensive.

The object of the present invention is to provide a method and an apparatus in which the above drawbacks are eliminated. A further object is to provide a method and an apparatus by means of which measuring of the properties of a moving paper web is fast and the measuring results are accurate and reliable.

The method of the invention is characterized in that the measurement is carried out as a reflection measurement and that the channels measuring different locations are calibrated by moving at least one reference sample across the path of the measuring beams in the cross direction of the paper web.

Further, the apparatus of the invention is characterized in that the measuring means comprises a transmitter and a receiver which are arranged on the same side of the paper web and that the apparatus comprises at least one reference sample that is movable across the path of the measuring beams in the cross direction of the paper web for calibrating the apparatus.

The basic idea of the invention is to measure at least one property of the paper web by measuring it at least at two locations in the cross direction of the paper web simultaneously and to calibrate the measuring means measuring different locations by moving at least one reference sample across the path of the measuring beams measuring different points in the cross direction of the paper web.

The invention has an advantage that the measuring channels of the measuring means can be calibrated or standardized on the same level simply and efficiently. The solution is very reliable and it improves the reliability and usability of the measurements considerably. A further advantage is that calibration can be performed while the web measurement is underway, because the calibration does not interfere with the measuring throughout the entire width of the paper web, since the reference sample is so small that in calibration it only covers the path of one or some of the measuring beams.

In the present specification, the term 'paper' refers to paper board and tissue, in addition to paper.

In the present specification, calibration refers to defining a quantity for a property of paper that is actually measured (temperature, etc.) The means for measuring the property must be properly calibrated so as to indicate the correct value of a stimulus measured. Thus all calibrated measuring means of the same type indicate the same measured value for the same measured stimulus.

However, several gauges are constructed such that a second property that has not been measured directly will be inferred on the basis of a first property by utilizing the correlation between the properties. For instance, several meters used in the paper industry direct the stimulus, such as radiant energy or a particle beam, at the paper whose properties are measured and then measure the modulated radiant flux or particle flux emitted by the paper. The mathematical relation describing the correlation between the properties obtained by these measurements is used for calculating the second property on the basis of the first property. The formula and parameters of this relation have to be previously known or predetermined. In some cases, the second property can be inferred on the basis of several measured properties by using a multivariable relation.

Because the strength or other properties of the source of stimulus may vary in various gauges or even in the same gauge with time, the correlation between the calibrated measurement and the property correlating therewith may vary in different gauges and at different times in the same gauge. Likewise, the correlation between the measured property and the correlating property may vary due to changes in other unmeasured properties. For instance, the correlation between microwave backscatter and sample moisture content changes if the sample contains carbon black.

Standardization is used for compensating for differences and changes in the stimulus or correlation. Standardization is also a means of calibration when the differences appearing in the stimulus or correlation are known or they are known to be insignificant.

In standardization, a property of at least one reference sample, whose one other property is known, is measured and a parameter representing the relation between the known property and the measured property is calculated for measuring means. A plurality of reference samples, one other property of each being known, are preferably used. If a plurality of reference samples, whose other known properties have different values, are used, it is possible to calculate a plurality of parameters for the relation. Thus, statistical methods, such as the method of least squares, can be used for calculating the most suitable parameters. By means of statistical methods, it is also possible to select the relation formula, in addition to other parameters.

Calibration is thus applied to properties that are measured directly and in connection wherewith a drift in the calibration of the measuring means is corrected. These properties include e.g. temperature and thickness of paper. Standardization is applied to properties that are measured indirectly and in connection wherewith one or more of the following features are simultaneously compensated for: i) differences in correlation between measured and inferred properties, ii) differences appearing in the stimulus used, iii) drift in the calibration of the measuring means. These properties include e.g. basis weight, moisture, ash content, colour, etc. For the sake of clarity, in the present specification, the term 'calibration' also refers to standardization, in addition to calibration.

BRIEF DESCRIPTION OF THE DRAWINGS

The invention will be described in greater detail in the attached drawing, wherein.

DETAILED DESCRIPTION OF PREFERRED EMBODIMENTS

Figure 1:
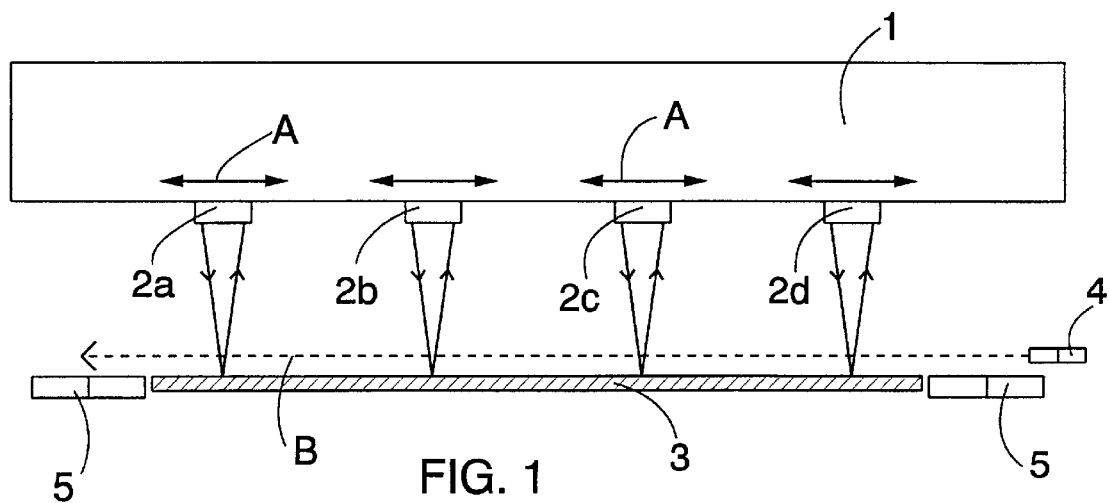
FIG. 1 is a schematic view of a measuring apparatus in accordance with the invention seen from the machine direction of the paper web.

FIG. 1 shows a measuring bar 1 which is installed across a paper web and onto which measuring means, i.e. sensors 2a to 2d, are secured. The sensors 2a to 2d measure properties of the paper web 3 simultaneously at adjacent locations such that the adjacent sensors 2a to 2d measure the same web property simultaneously. Thus, data on the properties of the paper web 3 is obtained quickly and on a large area. In the case of FIG. 1, the sensors 2a to 2d comprise both a transmitter and a receiver, whereby measuring is effected as a reflection measurement. If desired, the transmitter and the receiver can be placed on the opposite sides of the paper web 3, and then measuring is effected as a transmission measurement in a manner known per se. At its simplest, each sensor comprises one measuring channel, but the sensor may also comprise a plurality of measuring channels, for instance, in such a way that, in the sensor which measures spectrum, each different channel can measure a different wavelength of the same spectrum. Each measuring channel can also measure a specific spectrum. Different measuring channels of one sensor can measure simultaneously or successively by means of time multiplexing, for instance.

The apparatus also comprises a reference sample 4 which is movable along a path indicated by a broken line B in the cross direction of the paper web 3 across the beams measuring different measuring points. Calibration of said apparatus is thus carried out such that the reference sample 4 is moved through the measuring beam of each sensor 2a to 2d, and each sensor 2a to 2d is calibrated at the moment when the reference sample 4 coincides with the measuring beam. Each sensor 2a to 2d is then calibrated by the same reference sample 4, whereby their readings are made equivalent in a simple manner. Calibration is carried out such that the reference sample 4 having a given proportion or value for a measurable property is measured. If the reading of the sensor 2a to 2d differs from this value, it is adjusted so that the sensor 2a to 2d shows the correct value. If the reference sample 4 is shifted above the paper web 3 as shown in FIG. 1, i.e. on a different level than the web, the calibration can be carried out any time when needed, also during the paper making process. In that case, the measurements represent the common effect of the web and the reference sample, whereby these measurements, together with the measurements performed on the paper web alone, can be used for calibrating the sensors. Advantageously, when using the reference samples together with the paper web 3, said reference samples cause changes in measurements that exceed the expected changes in the paper web measurements during the measuring. If it is desired that the reference sample 4 travels on the same level with the paper web 3, the calibration has to be performed during a web break, when there is no paper web at all at the measuring location. Likewise, when using transmission measurement, the calibration has to be performed during a web break.

By means of the movable reference sample 4 it is also possible to monitor the condition of the measuring devices and particularly that of a single measuring channel. A range within which the reading of the measuring channel is normal, is determined for the measuring channel. If the reference sample 4 coincides with the measuring beam of the measuring channel and the reading of the measuring channel deviates considerably from normal, it is possible to conclude that there is something wrong with the measuring channel concerned. The solution can thus be used for fault diagnostics.

Figure 2:
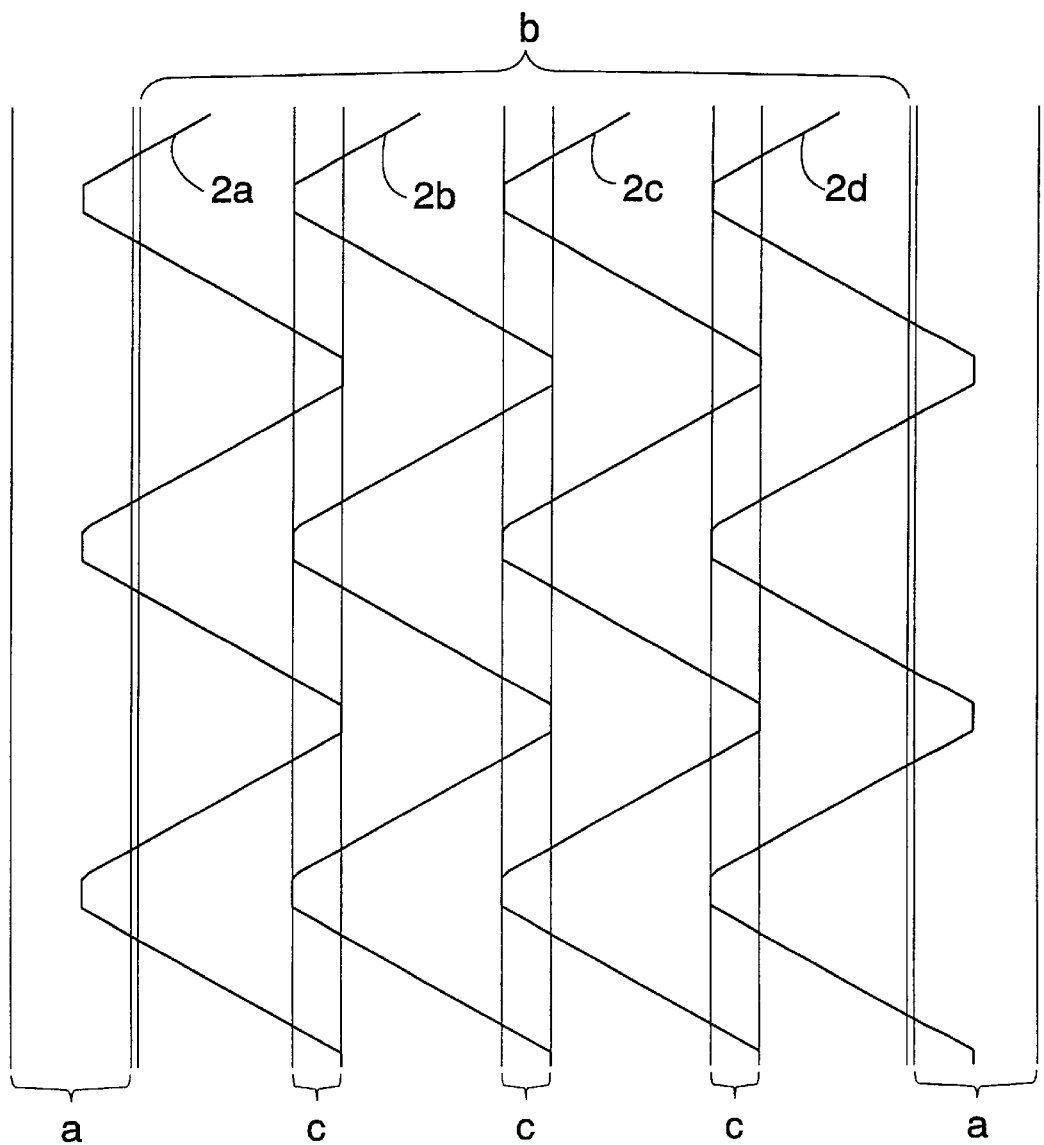
FIG. 2 is a schematic view of measuring paths of the measuring apparatus in FIG. 1.

The sensors 2a to 2d may be arranged to traverse a portion of the width of the paper web 3 in a reciprocating manner as indicated by arrows A. Measuring data are thus obtained simultaneously from several adjacent locations of the paper web 3, and moreover, measurements can be carried out alternately at every location across the paper web. This so-called mini-traversing has an advantage that not very many adjacent measuring channels are needed, but the paper web 3 can be measured considerably more accurately and quickly than with the commonly used one sensor that traverses the entire web. Sensor calibration by reference samples can be performed quickly either by means of the movable reference sample or by means of the edge reference samples 5 arranged at one or either edge of the paper web 3 as described above. In that case, the measuring paths of the sensors 2a to 2d are arranged as presented in FIG. 2. In FIG. 2, the band a depicts the location where the edge reference samples 5 are. Correspondingly, the band b depicts the paper web 3. For the sake of clarity, the band b of the paper web 3 and the bands a of the edge standards 5 are depicted in the same manner in FIG. 2, even though the edge reference samples 5 are typically stationary. The outermost sensors 2a and 2d are arranged to traverse such that they measure at least in part the paper web 3 and at least at some stage the reference sample 5. Further, the measuring paths of the adjacent sensors 2a to 2d are arranged such that they have a common band c, i.e. that their measuring areas partly overlap. In that case, calibration is carried out such that the outermost sensors 2a and 2d are calibrated by means of the edge reference samples 5. Thereafter is measured the reading of the sensor 2a on the common band c and the adjacent sensor 2b measures on the same band, whereby the adjacent sensor is calibrated by comparing the measuring results of the sensors. Said cycle is repeated on a next adjacent sensor as many times as necessary. This kind of calibrating measurement is preferably repeated several times in succession, whereby it is possible to compensate for errors that result from the adjacent sensors not measuring exactly the same location in the machine direction of the paper web 3 during the paper making process. The outermost sensors 2a and 2d need not necessarily travel over the edge reference samples 5 at other times than in calibration situations. Further, the measurements need not necessarily overlap at other times than in calibration. Furthermore, in measuring the sensors 2a to 2d can be mainly stationary, whereby they would traverse only in calibration. The edge reference samples may also be located elsewhere most of the time and they will be moved to the location shown in the figures only for the duration of calibration. The edge reference samples 5 can be utilized for the calibration of the apparatus during the paper making process both when using reflection measurement and transmission measurement.

Figure 3:
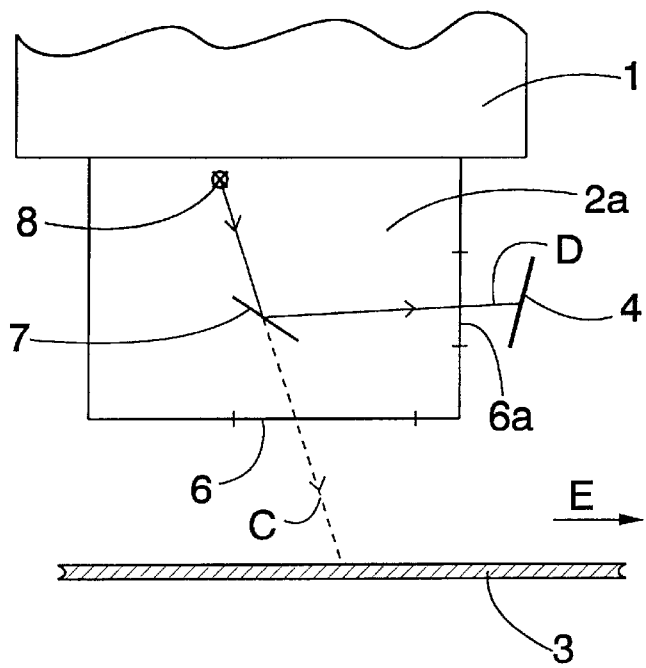
FIG. 3 is a schematic view of a second measuring apparatus in accordance with the invention seen from the machine direction of the paper web.

The reference sample 4 can be arranged to be movable in a manner shown in FIG. 3. In the case of FIG. 3, in a measuring situation, a measuring beam transmitted from a radiation source 8 propagates through a measuring window 6 of the sensor 2a to the paper web 3 as depicted by a broken arrow C. In a calibration situation, it is possible to divert the measuring beam with a means, such as a mirror 7, to control radiation to propagate along the arrow D and to hit the movable reference sample 4. The paper web moves in the direction of the arrow E and the reference sample 4 is shifted in the transverse direction with respect thereto. The mirror 7 and the reference sample 4 are arranged such that the distance proceeded by the measuring beam will not change, i.e. the optical distance between the mirror 7 and the paper web 3 is the same as the optical distance between the mirror 7 and the reference sample 4. The solution of FIG. 3 can be applied to measurements utilizing radiation, for instance optical or other electromagnetic measurements. This solution has an advantage that it can also be used during the paper making process, and nevertheless, no distance compensation is needed in the calibration. FIG. 3 depicts only the transmitted beam, but for instance in reflection measurement, the measuring beam preferably returns substantially along the same path as the transmitted beam. When the angle between the measuring beam C and the paper web 3 deviates from 90°, the effect of the mirror reflection on the measuring result can be eliminated. If desired, the reference sample 4 can also be positioned inside the sensor 2a, i.e. in the same housing with the measuring beam transmitter, and thus the reference sample 4 is protected from outside influences, for instance, fouling. On the other hand, a simple structural solution is to position the reference sample 4, in accordance with FIG. 3, outside the sensor 2a, whereby the beam indicated by the arrow D propagates through a side window 6a. Instead of using a means for controlling the beam, the travel of the measuring beam can be retained equal in an ordinary measuring situation and in calibration, for instance, by turning the beam-transmitting sensor by turning the measuring bar 1, for instance.

Figure 4:
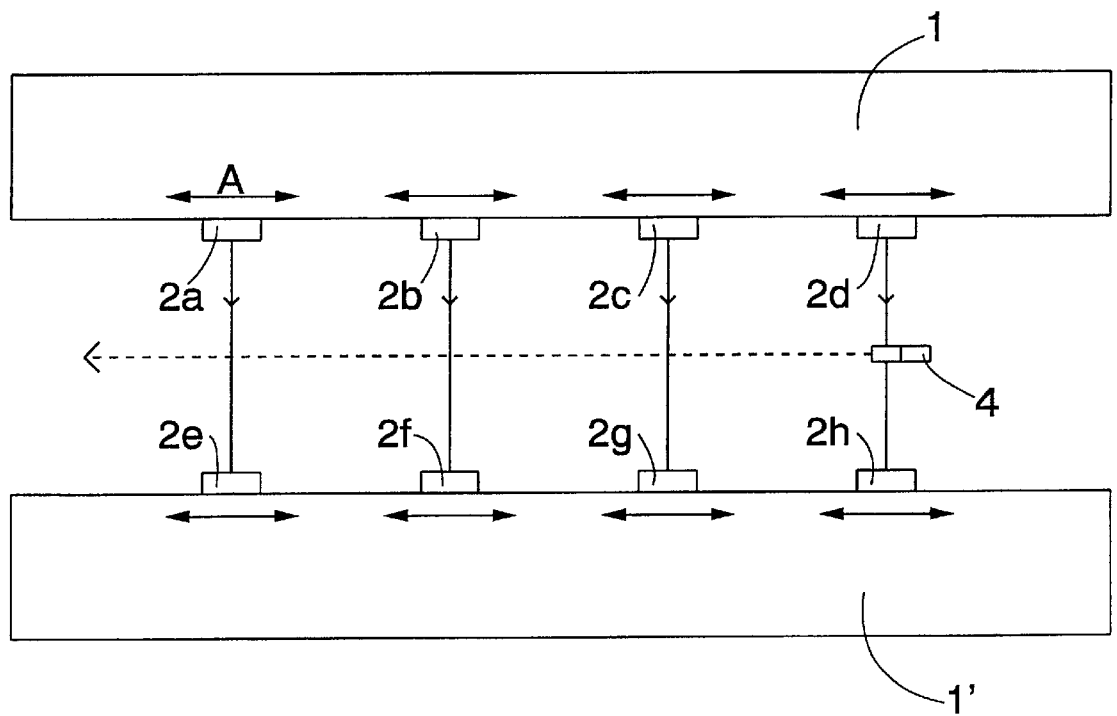
FIG. 4 is a schematic side view of a third measuring apparatus in accordance with the invention.

FIG. 4 shows a measuring arrangement operating on a transmission measurement principle. The sensors 2a to 2d transmit the measuring beams towards the paper web, and having passed through the web the modified beams arrive in sensors, in this case in a detector 2e to 2h. The sensors 2e to 2h are secured to the measuring bar 1', substantially at a corresponding location with the sensors 2a to 2d. The sensors 2e to 2h can also be moved a part of the width of the paper web 3 in the cross direction thereof. Thus the sensors 2a to 2d and 2e to 2h move substantially at the same time and at the same location. The reference beam 4 is shifted across the path of the measuring beams on the same level where the paper web 3 normally travels. Hence, the reference sample need not be compensated for distance, but calibration is simple to perform.

The reference sample 4 and the edge reference samples 5 are reference material with known properties. Further, the reference samples can consist of a plurality of different reference samples, when they have different reference sample sections for different proportions of the same property, for instance, for basis weights and other properties. Thus, when calibration is performed, from the reference sample is selected the section whose properties are closest to the properties of the paper web 3 to be measured, for instance, from the different sections are selected the one whose basis weight is closest to the basis weight of the paper web 3 to be measured. Absolute calibration can then be implemented. If the reference samples consist of a plurality of different sections, the properties of the different sections vary on an equally wide range as or on a wider range than the expected variation in a corresponding property of the paper web, whereby calibration for variation sensibility can be implemented. The reference sample may also have different reference sample sections for the calibration of different paper web properties, such as moisture and ash content measurements. Different sections of the movable reference sample 4 can be moved either with one traversing means or the different sections can be divided such that they are moved with a plurality of traversing means. The reference sample can be e.g. a transmission reference, an absorption reference or a reflection reference, when the reflection can be a mirror reflection or a diffusion reflection.

The reference sample 4 is so minuscule that in the calibration situation it covers the path of the measuring beam of only one sensor or some sensors 2a to 2d, for instance. Thus, when calibrating by means of the movable reference sample 4, only some of the sensors are excluded from measurement, while the others continue to measure in an ordinary manner. Furthermore, the calibration according to the invention is relatively quick to implement, since the calibration only takes the time which the reference sample 4 takes to traverse the paper web from edge to edge. Typically, the measuring devices are currently calibrated once in an hour, for instance. If necessary, the solution of the invention allows more frequent calibration, since the calibration is quick to carry out and it disturbs the ordinary measurements only for a relatively short period of time.

The adjacent measurements according to the invention can be implemented by using either a plurality of adjacent sensors or by measuring a plurality of different measuring points with one sensor, employing for instance one sensor that measures on a plurality of measuring channels simultaneously as described in U.S. Pat. No. 4,565,444, for instance. Further, in addition to mechanical traversing, measuring areas of adjacent sensors can be arranged to overlap by means of optical multiplexing, for instance.

The drawing and the related description are only intended to illustrate the inventive idea, and the details of the invention may vary within the scope of the claims.

What is claimed is:

1. A method for measuring properties of a paper web, comprising:
    performing a measurement of at least one property of the paper web at each of a plurality of locations in a cross direction thereof, the measurement at each location being performed with at least one measuring device that transmits a measuring beam at least on one measuring channel, and said locations in the cross direction of the paper web being measured simultaneously via respective measuring channels therefor, the measurements being carried out as reflection measurements, and wherein said measuring channels respectively measuring said locations are calibrated by traversing at least one reference sample in the cross direction of the paper web such that the reference sample is measured by the measuring beams.

2. A method as claimed in claim 1, wherein the reference sample is traversed on a different level than the paper web.

3. A method as claimed in claim 2, wherein the reference sample is traversed in the cross direction of the paper web during a paper making process and the measuring beam at each location is controlled to be directed along a path that is different in a calibration situation than in a measuring situation, such that in the calibration situation the measuring beam is controlled to hit the reference sample.

4. A method as claimed in claim 3, wherein the measuring beam in the calibration situation travels a distance from the at least one measuring device to the reference sample that is arranged to be substantially the same as a distance traveled by the measuring beam from the at least one measuring device to the paper web in the measuring situation.

5. A method as claimed in claim 1, wherein in a calibration situation the reference sample is traversed on a level along which the paper web travels in an ordinary measuring situation.

6. A method as claimed in claim 1, wherein the properties of the paper web are measured at least on two adjacent measuring channels that at least part of the time measure a common band of the paper web, wherein at least during calibration an edge reference sample is positioned at least at one edge of the paper web and an outermost one of the measuring channels measures a value of a property of the edge reference sample whereafter said outermost measuring channel measures a value of said property of the common band, and wherein measuring data from said measurements of the edge reference sample and common band is transferred to an adjacent one of the measuring channels which measures a value of said property of the common band for calibrating said adjacent measuring channel.

7. A method as claimed in claim 6, wherein the measuring channels are arranged in at least two adjacent measuring devices and wherein the adjacent measuring devices at least during calibration traverse at least a part of a width of the paper web in the cross direction.

8. A method as claimed in claim 1, wherein the reference sample comprises at least two different sections having different properties or different proportions of the same property.

9. A method as claimed in claim 1, wherein a normal range is determined for an output of the measuring channel, the reference sample is arranged to coincide with the measuring beam of the measuring channel and the output of the measuring channel is read, the output of the measuring channel is compared with the determined normal range and if the output deviates from normal by more than a predetermined amount a fault in connection with the measuring channel is detected.

10. A method as claimed in claim 1, wherein a plurality of adjacent measuring devices are arranged in the cross direction of the paper web.

11. A method as claimed in claim 1, wherein the measuring device traverses at least a portion of the width of the paper web in the cross direction.

12. An apparatus for measuring properties of a paper web, the apparatus comprising at least one measuring device having a transmitter for transmitting a measuring beam at least on one measuring channel and a receiver, the transmitter and the receiver being arranged on the same side of the paper web, the apparatus being arranged to measure at least one property of the paper web simultaneously on at least two measuring channels that are adjacent each other in a cross direction of the paper web, and further comprising at least one reference sample that is traversable in the cross direction of the paper web to carry the reference sample across a path of each of the measuring beams for calibrating the apparatus.

13. An apparatus as claimed in claim 12, wherein the reference sample is arranged to be traversed on a different level than the paper web.

14. An apparatus as claimed in claim 13, wherein the reference sample is arranged to be traversed in the cross direction of the paper web during a paper making process.

15. An apparatus as claimed in claim 14, wherein the apparatus comprises means for ensuring that a distance traveled by the measuring beam is substantially the same in a measuring situation as in a calibration situation.

16. An apparatus as claimed in claim 15, wherein the apparatus comprises a means for controlling the measuring beam in the calibration situation.

17. An apparatus as claimed in claim 16, wherein the means for controlling the measuring beam is a mirror.

18. An apparatus as claimed in claim 12, wherein the reference sample is arranged to be traversed on the same level as that of the paper web.

19. An apparatus as claimed in claim 12, wherein the apparatus comprises at least two adjacent measuring channels measuring the properties of the paper web and at least part of the time measuring a common band of the paper web, and further comprising an edge reference sample arranged at least at one edge of the paper web, wherein an outermost one of the measuring channels is arranged at least during calibration to measure a value of a property of the edge reference sample and thereafter a value of said property of the common band, and means for transferring measuring data from said measurements of the edge reference sample and common band to an adjacent one of the measuring channels which is arranged to measure a value of said property of the common band for calibrating said adjacent measuring channel.

20. An apparatus as claimed in claim 19, wherein the apparatus comprises at least two adjacent measuring devices, the measuring channels are arranged in the adjacent measuring devices, and the apparatus comprises means for making the adjacent measuring devices traverse at least a portion of a width of the paper web in the cross direction.

21. An apparatus as claimed in claim 12, wherein the reference sample comprises at least two different sections having different properties or different proportions of the same property.

22. An apparatus as claimed in claim 12, wherein there are a plurality of adjacent measuring devices in the cross direction of the paper web.

23. An apparatus as claimed in claim 12, wherein the apparatus comprises means for making the measuring device traverse at least a portion of the width of the paper web in the cross direction.

24. An apparatus for measuring properties of a traveling paper web, comprising:

a sensor assembly operable to transmit a plurality of measuring beams onto the paper web, the measuring beams impinging on the paper web at a plurality of locations along the paper web in a cross direction thereof, the sensor assembly being further operable to detect each measuring beam as affected by the paper web and to derive a value of a property of the paper web therefrom at each said location; and a reference sample traversable in the cross direction so as to be impinged by each measuring beam in sequence whereby a value of said property of the reference sample is derived for calibrating the sensor assembly, and wherein the reference sample is sized and arranged to be impinged by fewer than all of the measuring beams at all times during traversal of the reference sample in the cross direction, such that measurement of the paper web is carried out by at least one measuring beam at all times during said traversal.

25. The apparatus of claim 24, wherein the reference sample is traversed along a path different from that along which the paper web travels, and further comprising a mechanism for altering a path of each measuring beam such that the measuring beam is transmitted onto the reference sample when the reference sample is traversed.

26. The apparatus of claim 24, wherein the sensor assembly comprises a plurality of transmitters each operable to transmit a measuring beam onto the paper web, and a plurality of receivers for receiving beams resulting from the measuring beams transmitted onto the paper web.

27. The apparatus of claim 26, wherein the transmitters and receivers are on the same side of the paper web.

28. The apparatus of claim 26, wherein the transmitters and receivers are on opposite sides of the paper web.

29. A method for measuring properties of a traveling paper web, comprising:

transmitting a plurality of measuring beams from a sensor assembly onto the paper web such that the measuring beams impinge on the paper web at a plurality of locations along the paper web in a cross direction thereof, and detecting each measuring beam as affected by the paper web and deriving a value of a property of the paper web therefrom at each said location; and calibrating the sensor assembly by traversing a reference sample in the cross direction so as to be impinged by each measuring beam in sequence whereby a value of said property of the reference sample is derived and used for calibrating the sensor assembly, and wherein the reference sample is sized and arranged to be impinged by fewer than all of the measuring beams at all times during traversal of the reference sample in the cross direction, such that measurement of the paper web is carried out by at least one measuring beam at all times during said traversal.

* * * * *

UNITED STATES PATENT AND TRADEMARK OFFICE
CERTIFICATE OF CORRECTION

PATENT NO.     : 6,538,743 B2
DATED          : March 25, 2003
INVENTOR(S)    : Shakespeare et al.

It is certified that error appears in the above-identified patent and that said Letters Patent is hereby corrected as shown below:

<u>Title page,</u>
Item [75], Inventors, the second Inventor's name should read
-- Markku Mäntylä --.

Signed and Sealed this

Fifth Day of August, 2003

JAMES E. ROGAN
*Director of the United States Patent and Trademark Office*